United States Patent [19]

Comins

[11] Patent Number: 5,459,269
[45] Date of Patent: Oct. 17, 1995

[54] 14-HALO-CAMPTOTHECINS

[75] Inventor: Daniel L. Comins, Cary, N.C.

[73] Assignee: North Carolina State University, Raleigh, N.C.

[21] Appl. No.: 348,452

[22] Filed: Dec. 2, 1994

Related U.S. Application Data

[63] Continuation-in-part of Ser. No. 226,877, Apr. 12, 1994, Pat. No. 5,428,166, which is a continuation-in-part of Ser. No. 41,782, Apr. 1, 1993, Pat. No. 5,315,007, which is a continuation-in-part of Ser. No. 900,650, Jun. 18, 1992, Pat. No. 5,212,317.

[51] Int. Cl.$^6$ ................................................ C07D 491/22
[52] U.S. Cl. ................................................................ 546/48
[58] Field of Search ................................................ 546/48

[56] References Cited

U.S. PATENT DOCUMENTS

| | | | |
|---|---|---|---|
| 4,578,381 | 3/1986 | Uchida et al. | 514/233 |
| 4,894,456 | 1/1990 | Wall et al. | 546/41 |
| 5,162,532 | 11/1992 | Comins et al. | 546/48 |
| 5,191,082 | 5/1993 | Comins et al. | 546/116 |
| 5,212,317 | 5/1993 | Comins et al. | 546/301 |
| 5,243,050 | 9/1993 | Comins et al. | 546/116 |
| 5,342,947 | 8/1994 | Lackey et al. | 546/41 |

FOREIGN PATENT DOCUMENTS 0325247  7/1989  European Pat. Off. .

OTHER PUBLICATIONS

D. L. Comins and M. O. Killpack; *Lithiation of Methoxypyridines Directed by α–Amino Alkoxides*; The Journal of Organic Chemistry 55, pp. 69–73 (1990).
D. L. Comins and D. H. LaMunyon; *Orthos Lithiation of 2-, 3-, and 4-Methoxypyridines*; Tetrahedron Letters 29, pp. 773–776 (1988).
J. A. Bristol et al; *Sythetic Approaches to Camptothecin*; Abstracts, 23d International Congress of Pure and Applied Chemistry (Boston, Mass. 1971) pp. 67.
R. E. Lyle et al; *The Synthesis of an Analog of Camptothecin by a General Method*; J. Org. Chem. 38 No. 19; pp. 3268–3271 (1973).
D. L. Comins and J. D. Brown; *Ortho Metalation Directed by α–Amino Alkoxides*; The Journal of Organic Chemistry, 49, pp. 1078–1089 (1984).
D. L. Comins and J. D. Brown; *Ortho Sustitution of m–Anisaldehyde via α–Amino Alkoxide Directed Lithiation*; The Journal of Organic Chemistry 54, pp. 3730–3732 (1989).
J. A. Bristol et al; *Analogs of Camptothecin*; The Journal of Medicinal Chemistry 18 pp. 535–537, (1975).
E. Abramovitch; *Pyridine and its Derivatives; Heterocyclic Compounds*, 14, Suppl. Pt. 3; pp. 745–753 (1974).
T. Sugasawa et al; *Experiments of the Synthesis of dl–Camptothecin, II. Synthesis of a D–E Ring Analog of Camptothecin and a Total Synthesis of Ricinine*; Chem. Pharm. Bull 22, pp. 763–770 (1974).
J. J. Plattner, et al; *Synthesis of Some DE and CDE Ring Analogs of Camptothecin*; Journal of the American Chemical Society 94:24; pp. 8613–8615 (1972).
J. C. CAI and C. R. Hutchinson; *Camptothecin; The Alkaloids XXI*, pp. 101–137 (1983).
D. L. Comins; Ph.D. Thesis *"A Short Route to the D and E Rings"*; University of New Hampshire, Durham, New Hampshire pp. 25–29 (1977).
D. L. Comins; *A 10–Step Asymmetric Synthesis of (S) Camptothecin*; Journal of the American Chemical Society; pp. 10971–10972 (1992).
Nagata et al., J. Aichi Med. Univ. Assoc., vol. 11(3), pp. 286–293 (1983).

*Primary Examiner*—Bernard Dentz
*Attorney, Agent, or Firm*—Bell, Seltzer, Park & Gibson

[57] ABSTRACT

A method of making racemic DE ring intermediates for the synthesis of camptothecin and camptothecin analogs employing novel intermediates of Formula (XX) and (XXI):

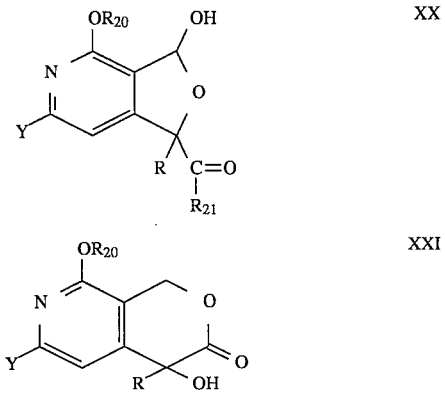

wherein $R_{20}$ is loweralkyl, R is loweralkyl, Y is H or halogen, and $R_{21}$ is loweralkoxy; as precursors to the DE ring intermediate.

The present invention also provides a camptothecin analog of Formula (I-A):

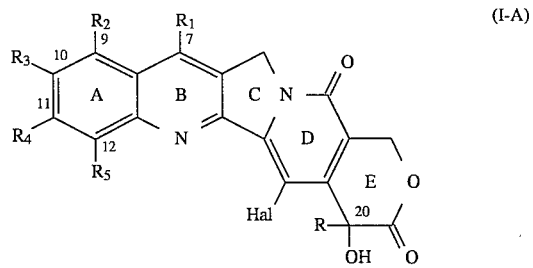

wherein:
  Hal is a halogen;
  and the remainder of the variables are as defined in the specification.

Additionally, other novel compounds useful in the preparation of the compounds of Formula (I-A) and methods of producing compounds of (I-A) are also provided.

8 Claims, No Drawings

14-HALO-CAMPTOTHECINS

RELATED APPLICATIONS

The instant application is a continuation-in-part of U.S. patent application Ser. No. 08/226,877, filed 12 Apr. 1994 now U.S. Pat. No. 5,428,166, which is a continuation-in-part of U.S. patent application Ser. No. 08/041,782, filed 1 Apr. 1993 now U.S. Pat. No. 5,315,007, which is a continuation-in-part of U.S. patent application Ser. No. 07/900,650, filed 18 Jun. 1992, now U.S. Pat. No. 5,212,317, the disclosures of which are incorporated herein by reference in their entirety.

FIELD OF THE INVENTION

The present invention relates to new methods of making racemic DE ring intermediates useful for the synthesis of camptothecin and camptothecin analogs.

BACKGROUND OF THE INVENTION

Camptothecin (Chem. Abstracts Registry No. 7689-03-4) is a naturally occurring compound found in *Camptotheca acuminata* (Nyssaceae) which has antileukemic and antitumor properties. Numerous camptothecin analogs having like properties are known, examples being those described in U.S. Pat. No. 4,894,456 to Wall et al. and European Patent Application No. 0 325 247 of Yaegashi et al.

A number of syntheses for camptothecin and camptothecin analogs are known. Most recently, parallel synthesis for camptothecin and camptothecin analogs have been disclosed in U.S. Pat. No. 5,162,532 to Comins and Baevsky. According to the methods disclosed therein, camptothecin and analogs thereof are prepared from the intermediates disclosed therein. One of the intermediates disclosed therein is the DE ring intermediate.

One method of synthesizing the DE ring intermediate was previously disclosed in Comins, D. L. The Synthesis of Analogs of Camptothecin, Ph.D. Thesis, University of New Hampshire, May 1977. A second method was disclosed in U.S. Pat. No. 5,162,532 to Comins and Baevsky. Subsequently, U.S. Pat. No. 5,212,3 17 to Comins and Baevsky, disclosed an alternate method of producing the DE ring intermediate.

An object of the present invention is to provide new methods for preparing DE ring intermediates, and novel intermediates useful for the preparation of such compounds, all of which are useful for the synthesis of camptothecin and camptothecin analogs.

SUMMARY OF THE INVENTION

The present invention provides a method of making compounds of Formula (XX) and (XXI):

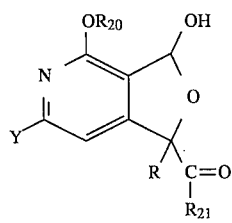
(XX)

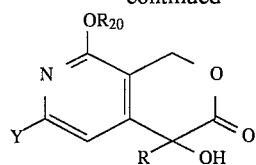
(XXI)

wherein $R_{20}$ is loweralkyl, $R_{21}$ is lower alkoxy, R is linear or branched loweralkyl, alkylaryl, hydroxyalkyl, or aryl; and Y is H or halogen. These compounds are useful in the preparation of compounds of Formula (III),

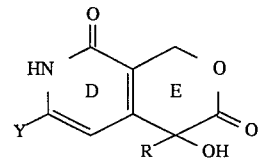
(III)

wherein R is linear or branched loweralkyl, alkylaryl, hydroxyalkyl, or aryl; and Y is H or halogen, which in turn is useful in the production of compounds of Formula (I):

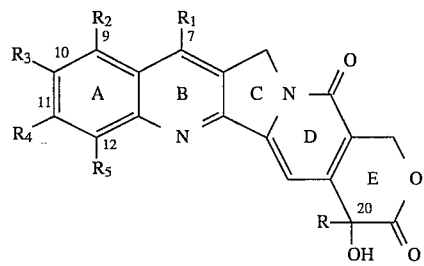
(I)

wherein:

R is linear or branched loweralkyl, alkylaryl, hydroxyalkyl, or aryl;

$R_1$ is H, linear or branched loweralkyl, loweralkoxy, alkylaryl, hydroxyalkyl, haloalkyl, aminoalkyl, dialkylamino, dialkylaminoalkyl, cycloaminoalkyl, aryl, aryloxy, C-glycal, $CO_2R$, nitro, cyano, halo, $SR_{23}$, $NR_{24}R_{25}$, or $OR_{26}$; and $R_2$, $R_3$, $R_4$, and $R_5$ are each independently selected from the group consisting of H, amino, hydroxy, loweralkyl, alkylaryl, hydroxyalkyl, haloalkyl, loweralkoxy, loweralkylthio, alkylamino, aminoalkyl, di(loweralkyl)amino, dialkylaminoalkyl, cycloaminoalkyl, aminoalkoxy, aryl, aryloxy, C-glycal, cyano, methylenedioxy, formyl, nitro, halo, azido, amido, hydrazino, any of the twenty standard amino acids bonded to the A ring via the amino-nitrogen atom, $SR_{23}$, $NR_{24}R_{25}$, or $OR_{26}$, or $R_3$ and R4 together form a 5- or 6- member aromatic, or dioxolane ring, (numbering in Formula I is by the Le Men-Taylor numbering system and rings are lettered in the conventional manner, see, U.S. Pat. No. 5,162,532 to Comins et al.); and wherein $R_{23}$, $R_{24}$, and $R_{22}$ are each independently selected from the group consisting of H, linear or branched alkyl, alkylaryl, hydroxyalkyl, aminoalkyl, acyl, or aryl; and $R_{26}$ is glycosyl.

In one embodiment illustrated by Scheme D,

Scheme D

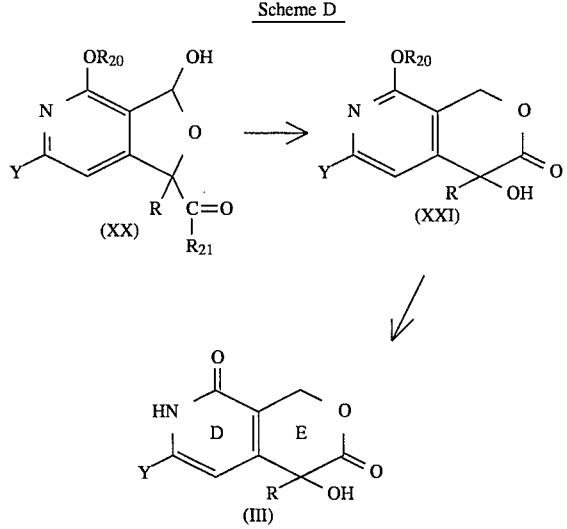

racemic compounds of Formula (III) are produced.

The present invention also provides a camptothecin analog of Formula (I-A):

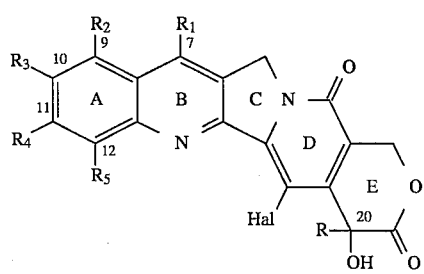

wherein Hal is a halogen, preferably selected from the group consisting of F, Cl, Br, and I; and R, $R_1$, $R_2$, $R_3$, $R_4$, and $R_5$ are as defined above for compounds of Formula (I).

The compounds of Formula (I-A) are prepared from the novel intermediate compounds of the present invention, namely the intermediates of Formula (IV-A):

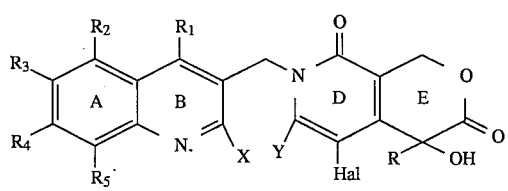

wherein Hal, R, $R_1$, $R_2$, $R_3$, $R_4$, and $R_5$ are as defined above for compounds of Formula (I-A), X is halogen, and Y is H or halogen;

which in turn are prepared from the novel intermediates of Formula (III-B):

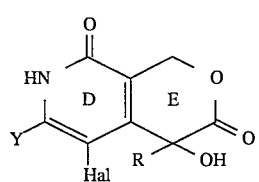

wherein Hal, R and Y are as defined above for compounds of Formula (IV-A).

The present invention also provides compounds of Formulas (I-A), (IV-A), and (III-B) wherein Hal is hydrogen or halogen, R is haloalkyl and $R_1$, $R_2$, $R_3$, $R_4$, $R_5$, X and Y are as defined above for compounds of Formula (I-A), (IV-A), and (III-B) respectively.

In one embodiment illustrated by Scheme E,

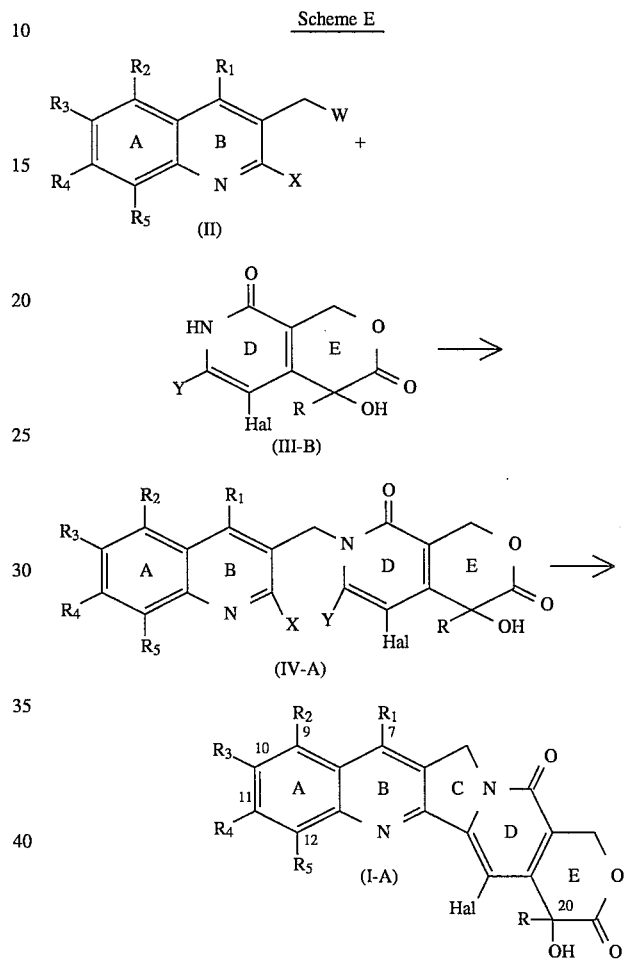

compounds of Formula (I-A) are produced.

DETAILED DESCRIPTION OF THE INVENTION

As used herein, the term "loweralkyl" means a linear or branched alkyl group with 1–8, preferably 1–4, carbon atoms, such as methyl, ethyl, propyl, isopropyl, n-butyl, tert-butyl, hexyl, and octyl. This definition also applies to a loweralkyl moiety in the loweralkoxy, loweralkylthio, and di(loweralkyl)amino groups. Thus, examples of loweralkoxy groups are methoxy, ethoxy, propoxy, sec-butoxy, and isohexoxy; examples of loweralkylthio groups are methylthio, ethylthio, tert-butylthio, and hexylthio; and examples of di(loweralkyl)amino groups are dimethylamino, diethylamino, diisopropylamino, di(n-butyl)amino, and dipentylamino.

The terms "halo" and "halogen" as used herein refers to a substituent which may be fluoro, chloro, bromo, or iodo.

The term "haloalkyl" as used herein refers to a linear or branched, saturated or unsaturated, alkyl substituted one or more times with one or more halogens. The preferred haloalkyls are linear or branched, saturated or unsaturated loweralkyls substituted one or more times with one or more halogens. As noted above, halogens include fluoro, chloro, bromo and iodo, preferably fluoro and chloro and more preferably fluoro. Examples of suitable haloalkyls include but are not limited to trifluoromethyl, pentafluoroethyl, trichloromethyl, and pentachloroethyl.

The compounds of Formula (III) above are, as noted above, prepared according to Scheme D below, Scheme D

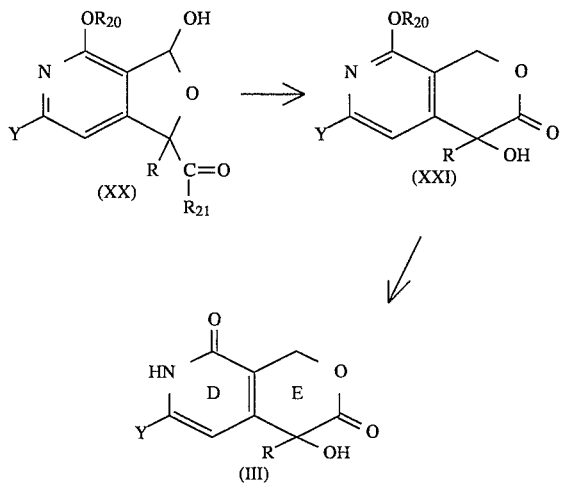

wherein $R_{20}$ is loweralkyl, $R_{21}$ is lower alkoxy, R is linear or branched loweralkyl, alkylaryl, hydroxyalkyl, or aryl; and Y is H or halogen.

Scheme D begins with the preparation of compounds of Formula (XX):

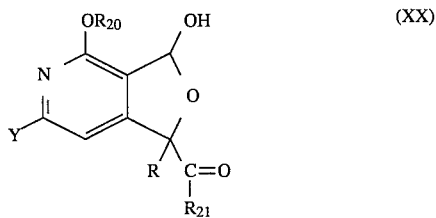

wherein:

$R_{20}$ is loweralkyl, preferably methyl; $R_{21}$ is lower alkoxy, preferably methoxy; R is linear or branched loweralkyl, alkylaryl, hydroxyalkyl, or aryl; preferably ethyl; and Y is H or halogen, preferably H.

The compounds of Formula (XX) are prepared by reacting an appropriate pyridine or substituted pyridine compound with mesityllithium, a formamide of ethylenediamine, and a base of the Formula $A^+B^-$, wherein $A^+$ is an inorganic cation, and $B^-$ is an organic anion.

The pyridine compound is preferably selected from the group consisting of 2-methoxypyridine and 5-chloro-2-methoxypyridine. The pyridine compound is initially reacted with mesityllithium or t-butyllithium. Mesityllithium may be prepared by reacting 2-bromomesitylene with t-butyllithium. The reaction of the pyridine with mesityllithium may be carried out in a suitable aprotic solvent such as tetrahydrofuran, ether or dimethoxyether, at variable temperatures ranging from between about −75° C. and about 37° C. over the course of the reaction. The resulting mixture is then reacted with a formamide of an ethylenediamine at a temperature of between about −75° C. and about 0° C. Suitable formamides of ethylenediamine include N-formyl-N,N',N' -trimethylethylenediamine and N-formyl-N,N',N' -triethylethylenediamine. The base of the Formula $A^+B^-$ is added at about −23° C. to form an intermediate.

The base $A^+B^-$ is a combination of an inorganic cation ($A^+$) and an organic anion ($B^-$). Exemplary inorganic cations include sodium, potassium, and lithium, with lithium being more preferred. Exemplary organic anions include propyl, n-butyl, t-butyl, s-butyl, phenyl, and n-pentyl, with n-butyl being preferred.

The intermediate formed by the addition of the base of Formula $A^+B^-$, is then reacted with anhydrous cerium trichloride. Anhydrous cerium trichloride can be prepared by heating hydrated cerium trichloride then drying further with an agent such as t-butyllithium. The anhydrous cerium trichloride is typically provided as a slurry in an aprotic solvent. Suitable aprotic solvents include tetrahydrofuran, ether and dimethoxyether, with tetrahydrofuran being preferred. The intermediate is typically reacted with anhydrous cerium trichloride at about −23° C.

The resulting mixture is further reacted with an alkyl α-ketobutyrate to produce the compound of Formula (XX). Exemplary alkyl α-ketobutyrates include methyl α-ketobutyrate, ethyl α-ketobutyrate, and t-butyl α-ketobutyrate, with methyl α-ketobutyrate being preferred. The reaction is typically carried out under variable temperatures ranging from between about −75° C. and about −23° C. The alkyl α-ketobutyrate is preferably added to the reaction solution rapidly, in a single aliquot. The compound produced is crystalline. Purification of the resulting compound of Formula (XX) can be accomplished by conventional methods known to those skilled in the art. A preferred method of purification is by radial PLC.

The compound of Formula (XX) is then reacted with a reducing agent in a polar solvent with heat, to yield the compound of Formula (XXI). Suitable reducing agents include aluminum isopropoxide, sodium borohydride, diisobutyl aluminum hydride, and sodium cyanoborohydride. Preferably the reducing agent is aluminum isopropoxide. Polar solvents include alkanols, with isopropanol being preferred. The reaction is typically carried out in an inert atmosphere, such as argon or nitrogen, at reflux for about 3 hours. The resulting compound of Formula (XXI) is then preferably isolated by extraction with a polar organic solvent. A preferred polar organic solvent is methylene chloride.

The thus produced compound of Formula (XXI) is then reacted with an inorganic acid and heat, to yield the compound of Formula (III). Exemplary inorganic acids include HCl, HBr, and HI. Preferably the reaction is heated at reflux for about 3 hours. Thereafter, the resulting crude compound of Formula (III) may be isolated by concentration in vacuo and the residue purified by any suitable means known to those skilled in the art. Exemplary means of purification include radial PLC and recrystallization. The reaction produces the compounds of Formula (III) in crystalline form.

When Y is halo in the compound of Formula (III), the compound may be hydrogenated by any suitable technique, preferably by catalytic hydrogenation in the presence of a palladium catalyst in a hydrogen atmosphere under pressure (e.g., at least three atmospheres), to remove the halogen. See generally, J. March, *Advanced Organic Chemistry* 510–511 (3d. Ed. 1985).

As another aspect, the present invention provides a new camptothecin analog of Formula (I-A):

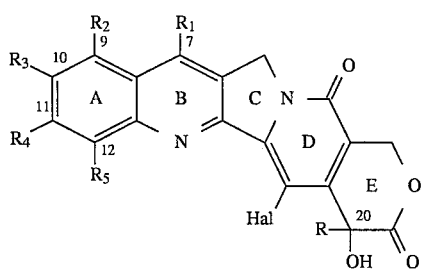

wherein:

Hal is a halogen, preferably selected from the group consisting of Cl, F, Br, or I; R is linear or branched loweralkyl, alkylaryl, hydroxyalkyl, or aryl, preferably linear alkyl, more preferably ethyl; $R_1$ is H, linear or branched loweralkyl, loweralkoxy, alkylaryl, hydroxyalkyl, haloalkyl, aminoalkyl, dialkylamino, dialkylaminoalkyl, cycloaminoalkyl, aryl, aryloxy, C-glycal, $CO_2R$, nitro, cyano, halo, $SR_{23}$, $NR_{24}R_{25}$, or $OR_{26}$; and $R_2$, $R_3$, $R_4$, and $R_5$ are each independently be H, amino, hydroxy, loweralkyl, alkylaryl, hydroxyalkyl, haloalkyl, loweralkoxy, loweralkylthio, alkylamino, aminoalkyl, di(loweralkyl)amino, dialkylaminoalkyl, cycloaminoalkyl, aminoalkoxy, aryl, aryloxy, C-glycal, cyano, methylenedioxy, formyl, nitro, halo, trifluoromethyl, azido, amido, hydrazino, any of the twenty standard amino acids bonded to the A ring via the amino-nitrogen atom, $SR_{23}$, $NR_{24}R_{25}$, or OR26; or $R_3$ and $R_4$ together form a 5- or 6-member aromatic, or dioxolane ring; and wherein $R_{23}$, $R_{24}$, and $R_{25}$ are each independently selected from the group consisting of H, linear or branched alkyl, alkylaryl, hydroxyalkyl, aminoalkyl, acyl, or aryl, and $R_{26}$ is glycosyl.

Preferably, $R_1$ is H, loweralkyl, aminoalkyl, dialkylamino, dialkylaminoalkyl, cycloaminoalkyl, loweralkoxy, and aryloxy. At least two of $R_2$, $R_3$, $R_4$, and $R_5$ may be H, and in a preferred embodiment, $R_2$, $R_4$, and $R_5$ are H. Preferably, $R_2$ is H or amino, $R_3$ is H or hydroxy, $R_4$ is H, and $R_3$ is H.

The compounds of Formula (I-A) are antineoplastic agents having antitumor and antileukemic activity. The compounds of Formula (I-A) are also useful for inhibiting topoisomerase enzymes, particularly topoisomerase I, in vitro and in vivo. The compounds of Formula (I-A) are useful for inhibiting the growth of leukemia cells such as L-1210 mouse leukemia cells and human KB cancer cells in vitro and in vivo. The compounds of Formula (I-A) are useful for inhibiting the growth of plants, such as corn and tobacco plants. The compounds of Formula (IA) are also useful as a chemosterilant for the housefly, *Dendrolimus puynctatus*. Additionally, compounds of Formula (I-A) wherein $R_1$ is halo are useful as intermediates for among other things, making compounds of Formula (I-A) wherein $R_1$ is loweralkyl.

The compounds of Formula (I-A) above may be prepared according to Scheme E below.

Scheme E

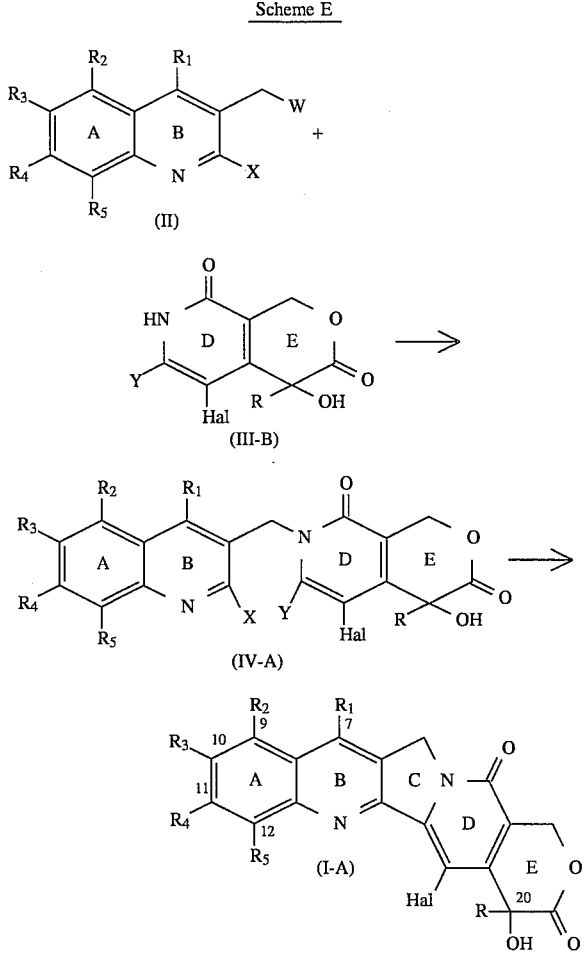

According to Scheme E, the compounds of Formula (I-A) are prepared from the compounds of Formula (IV-A):

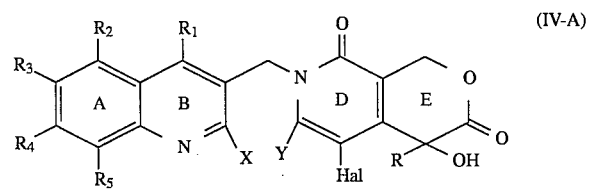

wherein Hal, R, $R_1$, $R_2$, $R_3$, R4 and $R_5$ are as defined above for Formula (I-A), X is halogen, and Y is H or halogen.

The compounds of Formula (I-A) are prepared by cyclizing the compounds of Formula (IV-A) by an intramolecular Heck reaction. The reaction is carried out in the presence of a palladium catalyst (e.g., palladium acetate) under basic conditions in a polar aprotic solvent such as acetonitrile or dimethylformamide. A phase transfer catalyst such as a tetraalkylammonium halide salt is preferably included. The reaction should be carried out in an inert atmosphere, such as under argon or nitrogen. The reaction mixture may be heated to a temperature between about 50° C. and about 100° C. for between about 1 and about 24 hours. Variations on these conditions will be apparent from the literature on the Heck reaction. See e.g., R. Grigg et al., *Tetrahedron* 46:4003 (1990).

As shown in Scheme E, the compounds of Formula (IV-A) are prepared from the novel intermediates of Formula (III-B):

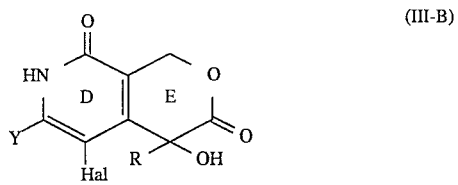

wherein:

Hal is a halogen, preferably selected from the group consisting of Cl, F, Br, and I; R is linear or branched loweralkyl, alkylaryl, hydroxyalkyl, or aryl, preferably linear alkyl, more preferably ethyl; and Y is H or halogen, preferably H. The compound of Formula (III-B) may optionally be provided in optically pure form, most preferably the (S) form, in accordance with know techniques. See, e.g., U.S. Pat. No. 5,258,516 to Comins and Baevsky, the disclosure of which is incorporated herein by reference in its entirety.

The intermediate of Formula (III-B) may be alkylated with a halomethylquinoline of Formula (II)

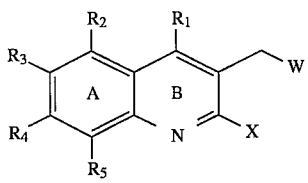

wherein $R_1$, $R_2$, $R_3$, $R_4$, and $R_5$, are as defined above for Formula (I-A), W is halogen, preferably chloro, and X is halogen, preferably bromo or iodo, to form the compounds of Formula (IV-A). The alkylation may take place in a suitable solvent, such as a polar protic solvent (e.g., isopropyl alcohol, ethanol, methanol), an aprotic solvent (e.g. 1,2-dimethoxyethane, tetrahydrofuran, toluene, acetonitrile, or dimethylformamide) or alternatively in an aqueous solution in the presence of a phase transfer catalyst. The reaction is preferably carried out under mildly basic conditions, to minimize attack on the pyridone ring oxygen. The reaction may be carried out in two stages by first forming the anion of the pyridone by addition of an alkali earth salt (e.g., potassium tert-butoxide) at about room temperature, and then adding the halomethylquinoline of Formula (II) to the reaction solution and heating the solution to between about 60° C. and about 100° C. for between about 4 and about 24 hours.

The compounds of Formula (III-B) may be prepared from the compounds of Formula (III). More specifically, the compounds of Formula (III-B) can be prepared by reacting the compounds of Formula (III) with a halogenating compound such as $Br_2$, $Cl_2$, $F_2$ and $I_2$, or a halosuccinimide. The particular halogenating compound or halosuccinimide employed depends on the desired halo substitution of the compound of Formula (Ill-B). Suitable halosuccinimides include N-chlorosuccinimide, N-bromosuccinimide, and N-iodosuccinimide. Typically, the reaction of the compound of Formula (III) with a halosuccinimide is carried out in a halogenated solvent such as chloroform, dichloroethane and carbon tetrachloride. The reaction mixture may be heated to a temperature of between about 60° C. and about 65° C. for between about 5 and about 75 hours, depending on the particular halo substitution sought. It will be readily apparent to one skilled in the art that the optimal parameters of the halogenation reaction will depend on the particular halogen substitution desired. The optimal parameters required for a particular substitution will be determinable by one skilled in the art without undue experimentation. The isolated compounds of Formula (III-B) may be purified by any suitable means known to those skilled in the art. Preferably, the compounds of Formula (III-B) are purified by radial PLC.

Alternatively, the present invention also provides compounds of Formulas (I-A), (IV-A), and (III-B) as given above, wherein Hal is hydrogen or halogen, R is haloalkyl and $R_1$, $R_2$, $R_3$, $R_4$, $R_5$, X and Y are as defined above for compounds of Formula (I-A), (IV-A), and (III-B) respectively. As used herein, the term "haloalkyl" has the same meaning as set forth above.

Compounds of Formula (III-B) wherein R is haloalkyl can be prepared according to methods disclosed herein for preparing compounds of Formula (III). More specifically, the compounds of Formula (III-B) wherein R is haloalkyl can be prepared from the intermediates (XX) and (XXI) as described above, with the exception that the compound of Formula (XX) is formed using an alkyl α-keto-halobutyrate (i.e., a halogenated alkyl α-ketobutyrate).

The compounds of Formula (III-B) wherein R is a haloalkyl can be used to prepare the compounds of Formula (IV-A) and (I-A) wherein R is haloalkyl, according to the methods described above. The compounds of Formula III-B and IV-A wherein Hal is hydrogen or halogen and R is haloalkyl are useful for the preparation of compounds of Formula I-A wherein Hal is hydrogen or halogen and R is haloalkyl. The compounds of Formula I-A wherein Hal is hydrogen or halogen and R is haloalkyl have the same utility as set forth above for compounds of Formula I-A. Specific examples of compounds of Formula (I-A) wherein R is haloalkyl include but are not limited to compounds wherein $R_1$, $R_2$, $R_3$, $R_4$, and $R_5$ are all H, Hal is H, and R is monochloroethyl, trichloroethyl, trifluoroethyl, pentachloroethyl and pentafluoroethyl.

In the Examples which follow, "mg" means milligrams, "g" means grams, "M" means Molar, ml means milliliter(s), "mmol" means millimole(s), "Bu" means butyl, "BuLi" means butyllithium, "THF" means tetrahydrofuran, EtOAc means ethyl acetate, EtOH means ethanol, MeOH means methanol, "min" means minutes, "°C." means degrees Centigrade, "p.s.i." means pounds per square inch, and "PLC" means preparative thin layer chromatography.

EXAMPLE 1

Preparation of
7-methoxycarbonyl-7-ethyl-9-hydroxy-7,
9-dihydrofurano[ 4, 5-c]-6-methoxypyridine Cerium trichloride heptahydrate (10.0g, 26.8 mmol) was placed in a dry 250-ml round-bottomed flask and heated at 145°–150° C. under vacuum (at less than 0.3 Torr) for 24 hours. Under a nitrogen atmosphere, the dry cerium trichloride powder was cooled to room temperature and suspended in THF (70 ml). The resulting slurry was stirred vigorously under nitrogen overnight. Immediately prior to use, the cerium trichloride slurry was titrated with t-BuLi until an orange coloration was achieved.

To a solution of t-BuLi (1.7 M/pentane, 18.0 ml, 30 mmol) in 70 ml of THF at −78° C. was added 1.82 ml (11.8 mmol) of 2-bromomesitylene. After stirring at −78° C. for 1 hour, a white heterogeneous mixture resulted. To this mixture was added 2-methoxypyridine (1.13 ml, 10.7 mmol) and stirring was continued at −78° for 1 hour, at 0° C. for 1 hour, and at room temperature for 1 hour. The mixture was cooled to −78° and N-formyl-N,N',N'-trimethylethylenediamine (1.5 ml, 14 mmol) was added dropwise. After stirring at −78° C. for 1 hour, the mixture was warmed to −23° C. and n-BuLi (2.0 M/hexane, 8.0 ml, 16 mmol) was added. The mixture was stirred at −23° C. for 2 hours to give a dark solution, which was transferred via a double tipped needle to the cerium trichloride slurry in THF at −23° C. After stirring at −23° C. for 2 hours, the homogeneous solution was cooled to −78° C., and methyl α-ketobutyrate (1.83 ml, 17.1 mmol) was added in one portion. The mixture was stirred at −78° C. for 1 hour and at 23° C. for 30 min. Glacial acetic acid (3.6 ml) was added at −23° C. and stirring was continued for 10 min. After addition of 10 ml of saturated aqueous sodium bicarbonate solution, the mixture was extracted with three 70-ml portions of methylene chloride. The combined organic layers were washed with water and brine, and were dried over magnesium sulfate. The product was concentrated under reduced pressure to give 4.5 mg of crude product, which was then purified by radial PLC (methylene chloride/hexanes/EtOAc, 1/1/0.1) to give 1.14 g (42%) of the lactol as a white solid. Analysis: mp 134°–135.5° C.; theory C 56.91, H 5.97, N 5.53; found C 57.18, H 6.05, N 5.26.

EXAMPLE 2

Preparation of 7-methoxycarbonyl-7-ethyl-9-hydroxy-7,9-dihydrofurano[4,5-c]-2-chloro-6-methoxypyridine Cerium trichloride heptahydrate (1.0 g, 2.68 mmol) was placed in a dry 25 ml round-bottomed flask and heated at 140° C. under vacuum (0.25 Torr) for 15 hours. Under a nitrogen atmosphere, the dry cerium trichloride powder was cooled to room temperature and suspended in THF (7 ml). The resulting slurry was stirred vigorously under nitrogen for 4 hours. The slurry was cooled to −78° C. and titrated with t-BuLi until an orange coloration was achieved. Meanwhile, to a solution (−78° C. ) of t-BuLi (0.6 ml, 1.18 mmol) and THF (7 ml) in another 25 ml flask was added 2-chloro-6-methoxypyridine (0.133 ml, 1.07 mmol), and the mixture was stirred at −78° C. for 1 hour. N-Formyl-N,N',N' trimethylethylenediamine (0.134 ml, 1.23 mmol) was added dropwise. After stirring at −78° C. for 1.5 hours, the reaction was warmed to −23° C. To the solution was added n-BuLi (0.85 ml, 1.6 mmol), and stirring was continued for 1.5 hour at −23° C. The red solution was transferred to the cerium trichloride slurry at −23° C. via cannula and stirred for 2 hours. The reaction mixture was cooled to −78° C. and methyl α-ketobutyrate (0.23 ml, 1.7 mmol) was added quickly. The reaction was stirred at −78° C. for 1 hour and at −23° C. for 30 minutes, quenched with AcOH (0.4 ml) at −23° C. , stirred for 10 minutes, and 0.7 ml of saturated sodium bicarbonate was added. The organic layer was separated and the aqueous layer was extracted with EtOAc. The combined organic extracts were washed with brine and dried over magnesium sulfate. Concentration gave the crude product which was purified by radial PLC (silica gel, 20% EtOAc/hexane) to give 52 mg (17%) pure product as a white solid. Analysis: mp 114°–115° C. (hexane); theory C 50.10, H 4.91, N 4.87; found C 50.20, H 4.92, N 4.84.

EXAMPLE 3

Preparation of 9-chloro-7-methoxypyrido[5,4-c]-2-oxo-3-ethyl-3-hydroxy-3,6-dihydropyran A mixture of the lactol of Example 2 (80 mg, 0.28 mmol) and aluminum isopropoxide (170 mg, 0.84 mmol) in isopropanol (anhydrous, 3.5 ml) was heated at reflux for 3 hours under nitrogen. The reaction was cooled to room temperature and stirred with 3 ml of saturated potassium sodium tartarate for 1 hour. The isopropanol was evaporated in vacuo, and the residue was extracted with methylene chloride. The extract was washed with brine and dried over magnesium sulfate. Concentration gave 65 mg of crude product. Purification by radial PLC (10% EtOAc/hexane) gave 52 mg of pure product (72%). Analysis: mp 159°–160° C. (hexane); theory: C 51.27, H 4.69, N 5.44; found C 51.17, H 4.71, N 5.40; $^1$H NMR (300 MHz, CDCl$_3$)δ7.20 (s, 1H), 5.53 (d, 1H, J=15.8 Hz), 5.23 (d, 1H, J=15.8 Hz), 4.00 (s, 1H), 1.79 (q, 2H, J=7.4 Hz), 0.96 (t, 3H, J=7.4 Hz); $^{13}$C NMR (75 MHz, CDCl$_3$) δ173.5, 158.3, 150.8, 148.9, 112.8, 109.8, 73.0, 65.2, 54.5, 31.7, 7.5; IR (KBr): cm$^{-1}$ 3483.5 (s), 3101.2 (s), 2962.5 (w), 1734.6 (s), 1600.4 (s), 1584.1 (s), 1460.4 (s), 1365.1 (s), 1154.5 (s), 1100.7 (s).

EXAMPLE 4

Preparation of 7-methoxypyrido[5,4-c]-2-oxo-3-ethyl-3-hydroxy-3,6-dihydropyran A mixture of 9-chloro-7-methoxypyrido[5,4-c]-2-oxo-3-ethyl- 3-hydroxy-3,6-dihydropyran (20 mg, 0.078 mmol) and sodium acetate (20 mg, 0.24 mmol) in 5 ml of EtOH was hydrogenated over 10% Pd/C (5 mg) at 42 p.s.i. for 10 hours at room temperature. The mixture was filtered through Celite and the solids were washed with MeOH. The filtrate was concentrated and the residue was purified by radial PLC (silica gel, 10% EtOAc/hexane) to give 15 mg (87%) of pure product as a white solid. Analysis: mp 107°–108° C. (hexane); $^1$H NMR (300 MHz, CDCl$_3$)δ: 8.19–8.21 (d, 1H, J=5 Hz), 7.15–7.17 (d, 1H, J=5 Hz), 5.55–5.61 (d, 1H, J=16 Hz), 5.24–5.29 (d, 1H, J=16 Hz), 3.99 (s, 3H),3.63(s, 1H), 1.76–1.83 (q, 2H, J=7 Hz), 0.93–0.98 (t, 3H, J=7 Hz); IR (KBr): cm$^{-1}$ 3478, 3140, 1735, 1603, 1458, 1398, 1380, 1231, 1159, 1102, 1035, 845.

EXAMPLE 5

Preparation of 7-oxopyrido[5,4-c]-2-oxo-3-ethyl-3-hydroxy-3,6-dihydropyran

A mixture of the lactol of Example 1 (47 mg, 0.186 mmol) and aluminum isopropoxide (114 mg, 0.558 mmol) in isopropanol (anhydrous, 2.5 ml) was heated at reflux for 3 hours under nitrogen. The cooled reaction mixture was stirred with 2.5 ml of saturated sodium potassium tartrate at room temperature for 1 hour. The reaction mixture was diluted with 10 ml of brine and then extracted with ether. The combined ether extracts were dried over magnesium sulfate and concentrated in vacuo to give 51 mg of 7-methoxypyrido[5,4-c]-2-oxo-3-ethyl-3-hydroxy- 3,6-dihydropyran as a yellow gum.

A solution of 51 mg of 7-methoxypyrido[5,4-c]-2-oxo-3-ethyl-3-hydroxy- 3,6-dihydropyran in 4 ml of 1N HCl was heated at reflux for 3 hours. The reaction mixture was concentrated in vacuo. The residue was purified by radial PLC (silica gel, 5 % MeOH/CH$_2$Cl$_2$) to give 22 mg (57% from lactol) of 7-oxopyrido[5,4-c]-2oxo-3-ethyl-3-hydroxy-3,6-dihydropyran as a white solid: mp 228°–229° C.

EXAMPLE 6

Preparation of 10-chloro-7-oxopyrido[5,4-c]-2-oxo-3-ethyl-3-hydroxy-3,6-dihydropyran A suspension of 7-oxopyrido[5,4-c]-2-oxo-3-ethyl-3-hydroxy-3,6dihydropyran (13 mg, 0.062 mmol), N-chlorosuccinimide (8.9 mg, 0.069 mmol), and CHCl$_3$(1 ml) was heated at reflux with vigorous stirring for 72 hours. Concentration gave the crude product which was purified by radial PLC (silica gel, 3% methanol/methylene chloride) to give 12 mg (80%) of pure product. Analysis: mp 209°–210° C. (CHCl$_3$); theory C 49.30, H 4.14, N 5.75; found C 49.13, H 4.26, N 5.65. $^1$H NMR (300 MHz, CDCl$_3$)δ: 7.49 (s, 1H), 5.55 (d, 1H, J=16.8 Hz), 5.13 (d, 1H, J=16.8 Hz), 3.9 (br s, 1H), 2.1–1.9 (m, 2H), 1.00 (t, 3H, J=7.4 Hz).

EXAMPLE 7

Preparation of 10-bromo-7-oxopyrido[5,4-c]-2-oxo-3-ethyl-3-hydroxy-3,6-dihydropyran A suspension of 7-oxopyrido[5,4-c]-2-oxo-3-ethyl-3-hydroxy-3,6-dihydropyran (13 mg, 0.062 mmol), N-bromosuccinimide (12.2 mg, 0.069 mmol), and CHCl$_3$ (1 ml) was heated at reflux with vigorous stirring for 9 hours. Concentration gave the crude product which was purified by radial PLC (silica gel, 3% methanol/methylene chloride) to give 17 mg (96 %) of pure product. Analysis: mp 173–174° C. (CHCl$_3$); theory C 41.69, H 3.50, N 4.86; found C 41.48, H 3.51, N 5.83. $^1$H NMR (300 MHz, CDCl$_3$) δ: 7.66 (s, 1H), 5.56 (d, 1H, J=16.8 Hz), 5.13 (d, 1H, J=16.8 Hz), 4.02 (br s, 1H), 2.1–1.9 (m, 2 H), 1.01 (t, 3H, J=7.5 Hz); $^{13}$C NMR (75 MHz, CDCl$_3$)δ: 172.8, 159.9, 147.0, 137.4, 121.4, 96.7, 73.3, 65.5, 31.8, 8.0.

EXAMPLE 8

Preparation of 10-iodo-7-oxopyrido[5,4-c]-2-oxo-3-ethyl-3-hydroxy-3,6-dihydropyran A suspension of 7-oxopyrido[5,4-c]2-oxo-3-ethyl-3-hydroxy-3,6dihydropyran (13.5 mg, 0.64 mmol), N-iodosuccinimide (22 mg, 0.098 mmol), and CHCl$_3$(2 ml) was heated at reflux with vigorous stirring for 3 days. Concentration gave the crude product which was purified by radial PLC (silica gel, 3% CH$_3$OH/CH$_2$Cl$_2$) to give 20 mg (92 %) of product as a yellow gum. $^1$H NMR (300 MHz, CDCl$_3$)δ: 7.83 (s, 1H), 5.55'5.61 (d, 1H, J=16 Hz), 5.07–5.13 (d, 1H, J=16 Hz), 3.89 (br s, 1H), 1.85–2.10 (m, 2H), 0.99–1.04 (t, 3H, J=7 Hz).

EXAMPLE 9

(S)-10-Chloro-7-oxopyrido[5,4-c]-2-oxo-3-ethyl-3-hydroxy-3,6-dithydropyran

A mixture of (S)-7-oxopyrido[5,4-c]-2-oxo-3-ethyl-3-hydroxy-3,6dihydropyran (70 mg, 0.335 mmol) and N-chlorosuccinimide (50 mg, 0.374 mmol) in 5 ml of 1,2-dichloroethane is heated at reflux with vigorous stirring for 17 hours. Concentration gave the crude product which can be purified by radial PLC (silica gel, 3% MeOH/CH$_2$Cl$_2$) to give 72 mg (88% ) of product as a white foam. Recrystallization of the purified product from toluene gives a white solid, mp 219–220° C. ; [α]$^{26}_D$+39.4 (c 1.0, MeOH).

EXAMPLE 10

(S)-8-(2'-Bromo-3'-quinolymethyl)-10-chloro-7-oxopyrido [5,4-c]-2-oxo-3-ethyl-3-hydroxy-3,6-dihydropyran To a stirred solution of (S)-10-chloro-7-oxopyrido[5,4-c] -2-oxo-3- ethyl- 3-hydroxy-3,6-dihydropyran (60 mg, 0.246 mmol) in 4 mL of 1,2-dimethoxyethane at 25° C. is added dropwise potassium tert-butoxide (1M in THF, 0.27 ml, 0.27 mmol). The resulting suspension is stirred at 25° C. for 30 min, then 2-bromo-3-bromomethylquinoline (96 mg, 0.319 mmol) is added neat, and the mixture is heated at reflux for 64 hours. The cooled reaction mixture is concentrated, and the residue is purified by radial PLC (silica gel, CH$_2$Cl$_2$, 1% MeOH/CH$_2$Cl$_2$, 2% MeOH/CH$_2$Cl$_2$) to give 102 mg (89%) of pure product as a colorless gum. Recrystallization of the purified product from CHCl$_3$/hexane gives a white solid, mp 149°–150° C. ; [α]$^{26}_D$+19.4(c 1.0, CHCl$_3$).

Analysis: High Resolution Exact Mass Measurement-EI: M$_{theoretical}$ 461.99820; M$_{sample}$ 462.00087. IR (CHCl$_3$): cm$^{-1}$ 1740, 1654, 1599, 1357, 1327, 1160, 1020. $^1$H NMR (CDCl$_3$, 300 MHz): δ 8.11 (s, 1H), 8.03–8.07 (d, 1H, J=8.6 Hz), 7.82–7.86 (d, 1H, J=8 Hz), 7.74–7.80 (t, 1H, J=15 Hz), 7.71 (s, 1H), 7.58–7.64 (t, 1H, J=15 Hz) 5.12–5.63 (2 AB Quartets, 4H), 3.84 (s, 1H), 1.90–2.20 (m, 2H), 0.97–1.03 (t, 3H, J=15 Hz). $^{13}$C NMR (CDCl$_3$, 75 MHz): δ172.73, 157.39, 148.07, 144.23, 142.08, 139.05, 137.07, 131.28, 128.38, 128.06, 127.87, 127.82, 126.99, 121.70, 110.64, 73.00, 66.23, 51.99, 32.11, 7.95.

EXAMPLE 11

(S)-14-Chlorocamptothecin

A mixture of (S)-8-(2'-bromo-3'-quinolylmethyl)-10-chloro-7oxopyrido[ 5,4-c]-2-oxo-3-ethyl-3-hydroxy-3,6-dihydropyran(30mg, 0.065 mmol), potassium acetate (19 mg, 0.194 mmol), tetrabutylammonium bromide (31 mg, 0.096 mmol) and palladium (II) acetate (3 mg, 0.013 mmol) in 3 ml of acetonitrile is heated at reflux for 7 hours under nitrogen. The hot reaction mixture is filtered through Celite. The residue is washed with hot CH$_2$Cl$_2$MeOH and the filtrate is concentrated in vacuo. The residue is purified by radial PLC (silica gel, CH$_2$Cl$_2$, 1% MeOH/CH$_2$Cl$_2$) to give 11 mg (44% ) of pure product as a light brown solid. Recrystallization from toluene gives light yellow crystals, mp 310–311° C. ; [α]$^{26}_D$+263.7 (C 0.12, CHCl$_3$/MeOH, 4:1).

IR(CHCl$_3$): cm$^{-1}$3501, 2921,2850, 1732, 1654, 1624, 1588, 1534, 1504, 1403, 1349, 1223, 1164, 1062. $^1$H NMR (300)MHz): δ5.39 (s,1H), 8.32–8.36 (d,1H, J=8.8 Hz), 7.91–7.95 (d, 1H, J=8 Hz), 7.81–7.87 (t, 1H , J=15 Hz), 7.66–7.72 (t, 1H, J=15 Hz), 5.71–5.78 (d, 1H, J=17 Hz), 5.21–5.37 (m, 3H), 4.02 (s, 1H), 2.05–2.36 (m, 2H), 1.02–1.08 (t, 3H, J=15 Hz).

The foregoing is illustrative of the present invention and is not to be construed as limiting thereof. The invention is defined by the following claims, with equivalents of the claims to be included therein.

That which is claimed is:

1. A compound of Formula (I-A):

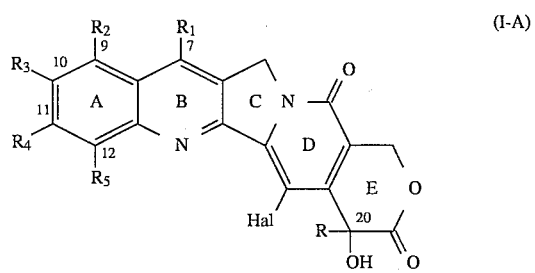

wherein:

Hal is a halogen;

R is linear or branched loweralkyl, alkylaryl, hydroxyalkyl, or aryl;

$R_1$ is H, linear or branched loweralkyl, loweralkoxy, alkylaryl, hydroxyalkyl, haloalkyl, aminoalkyl, dialkylamino, dialkylaminoalkyl, cycloaminoalkyl, aryl, aryloxy, C-glycal, $CO_2R$, nitro, cyano, halo, $SR_{23}$, $NR_{24}R_{25}$, or $OR_{26}$; and $R_2$, $R_3$, $R_4$, and $R_5$ are each independently selected from the group consisting of H, amino, hydroxy, loweralkyl, alkylaryl, hydroxyalkyl, haloalkyl, loweralkoxy, loweralkylthio, alkylamino, aminoalkyl, di(loweralkyl)amino, dialkylaminoalkyl, cycloaminoalkyl, aminoalkoxy, aryl, aryloxy, C-glycal, cyano, formyl, nitro, halo, azido, amido, hydrazino, any of the twenty standard amino acids bonded to the A ring via the amino-nitrogen atom, $SR_{23}$, $NR_{24}R_{25}$, or $OR_{26}$, or $R_3$ and $R_4$ together form a 5- or 6- member aromatic, or dioxolane ring; and wherein $R_{23}$, $R_{24}$, and $R_{25}$ are each independently selected from the group consisting of H, linear or branched alkyl, alkylaryl, hydroxyalkyl, aminoalkyl, acyl, or aryl; $R_{26}$ is glycosyl.

2. The compound according to claim 1, wherein Hal is selected from the group consisting of Cl, F, or Br.

3. The compound according to claim 1, wherein R is ethyl.

4. The compound according to claim 1, wherein $R_1$ is H.

5. The compound according to claim 1, wherein at least two of $R_2$, $R_3$, $R_4$, and $R_5$ are H.

6. The compound according to claim 1, wherein $R_2$ is selected from the group consisting of H and amino, $R_3$ is selected from the group consisting of H and hydroxy, $R_4$ is H, and $R_5$ is H.

7. The compound according to claim 1, wherein R is ethyl, $R_1$ is H, $R_2$ is H, $R_3$ is H, $R_4$ is H, and $R_5$ is H.

8. The compound according to claim 1, wherein $R_1$ is selected from the group consisting of loweralkyl, aminoalkyl, dialkylamino, dialkylaminoalkyl, and cycloaminoalkyl.

* * * * *